United States Patent [19]

Mizui et al.

[11] Patent Number: 4,980,507
[45] Date of Patent: Dec. 25, 1990

[54] PROCESS FOR PRODUCING POLYETHYLENEPOLYAMINE

[75] Inventors: Norimasa Mizui; Keiji Mitarai; Yukihiro Tsutsumi, all of Yamaguchi, Japan

[73] Assignee: Tosoh Corporation, Yamaguchi, Japan

[21] Appl. No.: 361,665

[22] Filed: May 30, 1989

Related U.S. Application Data

[63] Continuation of Ser. No. 871,172, Jun. 3, 1986, abandoned, which is a continuation of Ser. No. 518,260, Jul. 28, 1983, abandoned.

[30] Foreign Application Priority Data

Jul. 28, 1982 [JP] Japan .................. 57-130276

[51] Int. Cl.$^5$ ............... C07C 85/04; C07C 87/16; C07C 87/20
[52] U.S. Cl. ................................................. 564/482
[58] Field of Search ......................... 564/482

[56] References Cited

U.S. PATENT DOCUMENTS 2,769,841 11/1956 Dylewski et al. .................. 564/482
3,484,488 12/1969 Lichtenwalter et al. ........... 564/482
3,751,474 8/1973 Phillips et al. ...................... 564/482
4,404,405 9/1983 Winters ............................... 564/482

FOREIGN PATENT DOCUMENTS 740751 6/1980 U.S.S.R. ............................ 564/482

Primary Examiner—J. E. Evans
Attorney, Agent, or Firm—Sughrue, Mion, Zinn, Macpeak & Seas

[57] ABSTRACT

A process for producing polyethylenepolyamine from ethylene dichloride and aqueous ammonia which comprises reacting ethylene dichloride with ammonia, and then continuing the reaction in the presence of at least one kind of amine when the overall conversion of ethylene dichloride has become 25 to 85%.

7 Claims, 1 Drawing Sheet

PROCESS FOR PRODUCING POLYETHYLENEPOLYAMINE

This is a Continuation, ( ) Division of application Ser. No. 06/871,172 filed June 3, 1986, which is a Continuation of application Ser. No. 06/518,260 filed July 28, 1983 both now abandoned.

FIELD OF THE INVENTION

The present invention relates to a process for producing polyethylenepolyamine of high molecular weight by the reaction of ethylene dichloride (abbreviated as EDC hereinafter) and ammonia. More particularly, the invention relates to a process for producing polyethylenepolyamine of high molecular weight from EDC and aqueous ammonia in such a manner that when EDC has reached a proper level of reaction, the reaction is continued in the presence of amine. The process is economical and provides a product of high quality.

BACKGROUND OF THE INVENTION

It has long been known that ethyleneamines are produced by the reaction of EDC and aqueous ammonia. The reaction product thus formed as a mixture of several tens of ethyleneamines including linear, branched, and cyclic amines. They are separated into ethylenediamine (EDA), piperazine (P), diethylenetriamine (DETA), N-aminoethylpiperazine (N-AEP), triethylenetetramine (TETA), tetraethylenepentamine (TEPA), and pentaethylenehexamine (PEHA) by distillation or other means. Among these ethyleneamines, EDA, P, DETA, and N-AEP which have two or three nitrogen atoms in the molecule are available in the comparatively pure form. Other amines (TETA, etc.) having four or more nitrogen atoms are mixtures composed of linear, branched, and cyclic amines.

In the production of polyethylenepolyamines having four or more nitrogen atoms, isomeric branched amines in addition to linear amines are formed as by-products. In the production of EDA and DETA, P and N-AEP are formed as by-products, respectively. Likewise, in the production of amines having four or more nitrogen atoms, at least two kinds of cyclic amines having a piperazine ring (as represented by the formulae below) are easily formed as by-products.

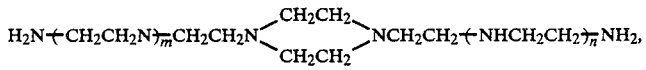

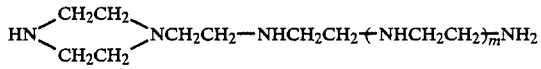

(where m and n are integers of 0 to 4).

These linear, branched, and cyclic amines having the same number of nitrogen atoms cannot be separated by the usual means because their boiling points are close to one another.

Among these ethyleneamines, EDA is used as the raw material of agricultural chemicals, rubber chemicals, EDTA, polyethers, and others; DETA is used as a paper strengthening agent and surface active agent; and polyethylenepolyamines including DETA are used for polyamide resins, epoxy resin hardeners, and lubricant additives. What is important to note is that the ethyleneamines used for these applications should contain many active hydrogen atoms. In other words, the polyamines, which are mixtures of linear, branched, and cyclic compounds, should contain as much linear amines as possible, and as little cyclic amines as possible.

Recently, the supply of polyamines including DETA is short, whereas the supply of EDA is excessive. This is caused by the fact that it is difficult to produce polyamines of high quality. On the other hand, in the production of ethyleneamines by the reaction of EDC and aqueous ammonia, ammonia is used in large excess of EDC, and therefore, it is necessary to recover and recycle the excess ammonia, and to distill away a large amount of water brought into the reaction system in the form of aqueous ammonia.

For correction of the above-mentioned unbalanced demand-supply situation of amine, there has been a strong desire for a process for economically producing polyamines of high quality.

It is known, as disclosed in U.S. Pat. Nos. 2,049,467, 2,760,979, and 2,769,841; British Patent No. 1,147,984, etc., that ethyleneamines are formed in varied ratios depending on the molar ratio of ammonia and EDC, and the reaction conditions such as concentrations of aqueous ammonia, reaction temperature, and additives used. So far, there is no satisfactory process for economically producing polyamines of high quality.

According to the following patents, polyamines including DETA are obtained in an amount (by weight) equal to or more than that of EDA.

(1) U.S. Pat. No. 2,049,467

Ammonia (4.9% aqueous ammonia) and EDC are reacted in a molar ratio of 2.77 in the presence of 19.4 times as much water as ammonia and 9.2 times as much water as EDC, at a reaction temperature of 140° to 150° C., to give EDA 40% and polyamines 60% (DETA 30%, TETA 20%, and higher amines 10%).

(2) U.S. Pat. No. 2,769,841

Ammonia (35% aqueous ammonia) and EDC are reacted in a molar ratio of 5.7 at a reaction temperature of 150° to 225° C., to give EDA 30.6% and polyamines 62.4% (TETA 30.5% and TEPA 31.9%). During the reaction, DETA formed is recycled, together with aqueous ammonia, in an amount of about 0.5 mol for 1 mol of EDC, to the reactor.

(3) U.S. Pat. No. 3,484,488

Ammonia (65% aqueous ammonia) and EDC are reacted in a molar ratio of 15 at a reaction temperature of 90° to 100° C. During the reaction, EDA, DETA, or TETA formed is recycled, so that the formation of the recycled amine is reduced and the formation of polyamines having higher molecular weight than the recycled amine is increased.

The above-mentioned processes have the following disadvantages.

According to the process (1), polyamines are formed in a large amount, but a large quantity of water is required. Removal of water after reaction needs a large quantity of energy. Thus, this process is economically unfavorable.

According to the processes (2) and (3), the yield of polyamines is effectively increased by recycling the formed amine. However, the process (2) has some disadvantages; that is, the reaction temperature is so high that EDC reacts so rapidly with ammonia or formed amine. Consequently, it is very difficult to remove and control reaction heat (exothermic reaction). Moreover, the formed amine decomposes when the reaction temperature rises above 250° C. The reaction of EDC and ammonia generates heat as much as about 40 kcal/mol. If ammonia is reacted with EDC in a molar ratio smaller than 10 and at a reaction temperature higher than 130° C., the reaction takes place rapidly with a large quantity of heat. The heat can be removed and the temperature can be controlled only by using a tank reactor or column reactor having a heat exchanger with a very large heat transfer area, or by using a multi-tubular reactor. These reactors are expensive and have the following disadvantages.

The tank reactor consumes a great deal of power for the stirrer or circulating pump, and tends to form cyclic amines as by-products.

The multi-tubular reactor tends to cause channelling and clogging with resinous by-products.

In the above-mentioned patent (3), recycling of amine is described; but the quantity for recycling is based on very unstable γ-chloroethylamine and the method for analyzing it is not disclosed. Therefore, the process disclosed in this patent is impossible to practice.

In order to overcome the above-mentioned disadvantages involved in the conventional processes, the present inventors carried out extensive studies on the process for economically producing polyethylenepolyamine of high quality. As the result, it was found that the object can be achieved by using EDC and aqueous ammonia as the raw materials and continuing the reaction in the presence of amine when the reaction of EDC and ammonia has proceeded to a proper extent. The present invention is based on these findings.

SUMMARY OF THE INVENTION

Accordingly, it is an object of this invention to provide a process for producing polyethylenepolyamine from EDC and aqueous ammonia which comprises reacting EDC with ammonia, and then continuing the reaction in the presence of at least one kind of amine when the overall conversion of EDC has reached an appropriate region and taking the reaction to completion.

The amines includes ethyleneamines such as EDA, DETA, TETA, TEPA, and PEHA; and primary and/or secondary aliphatic amines such as propanediamine, aminopropylethylenediamine, bis-aminopropylethylenediamine, hexamethylenediamine, monoor diethanolamine, and aminoethylethanolamine. Preferable among them are ethyleneamines, and more preferable is ethylenediamine.

The term "overall conversion of EDC" used herein means a sum of a percent conversion of EDC initially fed to the reaction system and a percent conversion of EDC fed after the addition of amine to the reaction system.

DETAILED DESCRIPTION OF THE INVENTION

Figure 3:
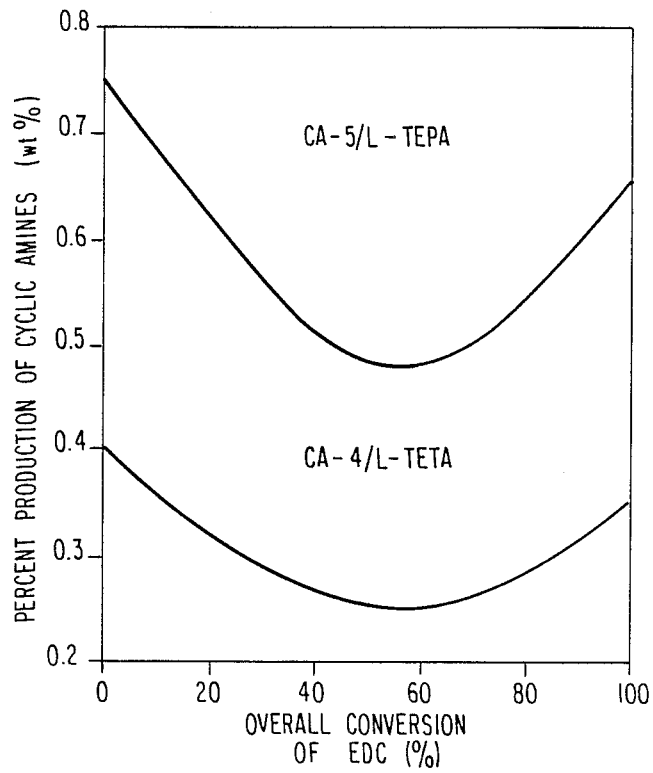
FIG. 3 is a graph showing the overall conversion of EDC at the time of EDA addition vs. the formation of cyclic amines as by-products. The relationships as shown in FIG. 3 are those obtained in the same manner as in Example 1.

The present invention utilizes a unique phenomenon which takes place when EDC and ammonia are reacted in the presence of at least one kind of amine. If the reaction of EDC and ammonia is carried out in the presence of amine, the quantity of cyclic amines which are formed in TETA and TEPA as by-products greatly varies depending on the overall conversion of EDC at which the amine is caused to be present, as shown in FIG. 3.

The present invention is, therefore, to provide a process for producing polyethylenepolyamines of high quality by reacting EDC with ammonia, and then continuing the reaction in the presence of at least one kind of amine when the overall conversion of EDC has reached 25 to 85%, preferably 30 to 80%, more preferably 35 to 70%, and taking the reaction to completion.

If the overall conversion of EDC is below 25%, although the ratio of polyamines formed (excluding EDA, P and N-AEP) to EDA, PA/EDA, is high, the polyamines formed are not satisfactory in quality because the amount of cyclic amines also formed is large. On the other hand, if it exceeds 85%, such is not desirable because the PA/EDA is low and the amount of cyclic amines formed is increased.

In a preferred embodiment of this invention, the reaction is carried out stepwise by feeding EDC in two or more portions. In this case, the ratio of EDC to be fed in proportions must be changed under the overall conversion of EDC as described above. This method is advantageous in that reaction heat can be controlled easily and that the ratio of polyethylenepolyamines can be adjusted by changing the ratio of EDC to be fed in proportions. Therefore, it can be said that this method is a useful and practical method in adjusting the ratio of polyethylenepolyamines rather than a method in which the time of addition of amine is changed when EDC is fed at one time. The advantages of this method are shown in Table 1 below. These relationships as shown in Table 1 are those obtained in the same manner as in Example 5 except for changing the ratio of EDC to be fed in two proportions.

TABLE 1

| Ratio of EDC (1st feed/2nd feed) | 80/20 | 55/45 | 30/70 |
|---|---|---|---|
| Overall Conversion of EDC at the Time of EDA Addition (%) | ca. 80 | ca. 55 | ca. 30 |
| % Products EDA | 42.9 | 26.8 | 12.1 |
| DETA | 26.3 | 31.7 | 35.4 |
| TETA | 14.2 | 18.4 | 21.7 |
| TEPA | 5.9 | 8.2 | 10.3 |
| PEHA & Higher | 5.2 | 8.0 | 12.2 |
| P | 2.2 | 2.7 | 3.0 |
| N-AEP | 3.4 | 4.2 | 5.3 |
| PA/EDA | 1.2 | 2.5 | 6.6 |
| CA-4/L-TETA | 0.27 | 0.25 | 0.31 |
| CA-5/L-TEPA | 0.57 | 0.52 | 0.61 |

In a more preferred embodiment of this invention, the above-mentioned reaction is carried out adiabatically or isothermally.

The adiabatic reaction as used in this invention means a manner of reaction in which the reaction system is not heated or cooled intentionally; but natural heat dissipation from the equipment is not taken into account. This process has great advantages in that the formation of cyclic amines as by-products is reduced to an extreme extent, the problem of reaction heat is solved completely, and the clogging of equipment does not occur.

The isothermal reaction as used in this invention means a manner of reaction in which the reaction temperature is kept constant by heating or cooling the reaction system.

The advantages of this invention are listed below.

(1) The formation of cyclic amines as by-products is small.

(2) The production ratio of polyamine is high.

(3) The requirement of ammonia and water is small, and energy consumption is small.

(4) The formation of resinous substance as a by-product is very small, and clogging of apparatus with resinous substance does not take place.

(5) The reaction is carried out at a comparatively low temperature, and the loss of formed amine due to thermal decomposition is small.

The invention is described with reference to FIGS. 1 and 2.

According to this invention, it is not necessarily required to feed EDC in portions, but it is preferable to feed EDC in portions. The reaction may be carried out continuously or batchwise, and the reactor may be of a single-tubular type or a multi-tubular type, or a tank reactor or column reactor. The continuous reaction in a single-tubular reactor is most simple and economical.

Figure 1:
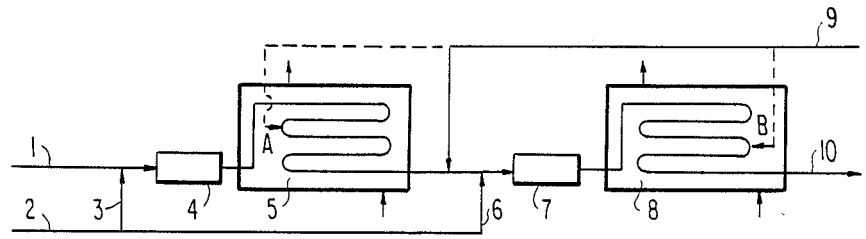
FIG. 1 is a flow sheet of an isothermal reaction process.

FIG. 1 shows the flow sheet of isothermal reaction in which EDC is fed in two portions. Aqueous ammonia is introduced from a pipe 1, and EDC is introduced from a pipe 2. EDC is split into two portions, one of which is fed to a mixer 4 from the pipe 3 together with aqueous ammonia from the pipe 1. After thorough mixing, EDC and ammonia are introduced into a first isothermal reactor 5. The reaction product discharged from the reactor 5 is introduced into a mixer 7 together with the remaining EDC introduced through a pipe 6. After thorough mixing, both are introduced into a second isothermal reactor 8 in which the reaction is completed. An amine is added through a pipe 9 to at least one point between point A where the overall conversion of EDC fed from the pipe 2 reaches 25% and point B where the overall conversion of EDC reaches 85%. The overall conversion may be replaced by the reaction time if the relationship between the overall conversion of EDC and the reaction time after EDC feeding is previously obtained at different reaction temperature.

Where EDC is fed in three or more portions, the mixer and isothermal reactor should be added, as many as necessary according to the number of portions, after the isothermal reactor 5 or 8, and each portion of EDC should be introduced into each mixer. The split portion of EDC should be fed to a point where the previously fed EDC is converted to 50 to 100%, and preferably 80 to 100%. The reaction mixture discharged through a pipe 10 from the final reactor 8 is treated as usual (such as addition of alkali, separation and recovery of excess ammonia, separation of sodium chloride, dehydration, and fractional distillation), and the desired polyethylenepolyamine is obtained.

The preferred concentration of aqueous ammonia introduced through the pipe 1, and the preferred molar ratio of EDC introduced through the pipe 2 to ammonia introduced through the pipe 1 slightly vary depending on the number of portions of EDC and the reaction temperature in each isothermal reactor.

The preferred reaction temperature in each isothermal reactor slightly varies depending on the number of portions of EDC. It is 60° to 250° C., and preferably 80° to 150° C., where EDC is fed in two portions; and it is 60° to 180° C., and preferably 80° to 150° C., where EDC is fed in three portions.

Amine introduced through the pipe 9 is added to EDC introduced through the pipe 2 in a molar ratio of 0.1 to 2.0, and preferably 0.1 to 1.0. As the ratio of amine added is increased, the formation of the same amine as that added is suppressed and the formation of polyamines having a higher molecular weight than that of the amine added is promoted.

Figure 2:
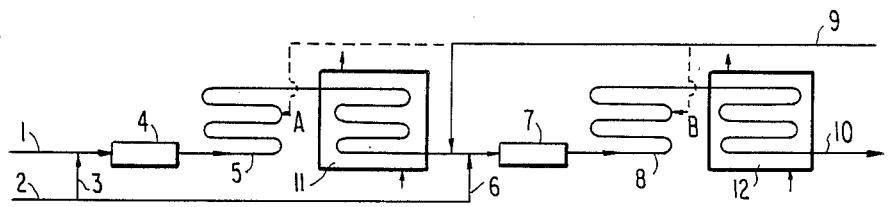
FIG. 2 is a flow sheet of an adiabatic reaction process and the schematic representation of temperature change in the adiabatic reaction process.
Figure 2:
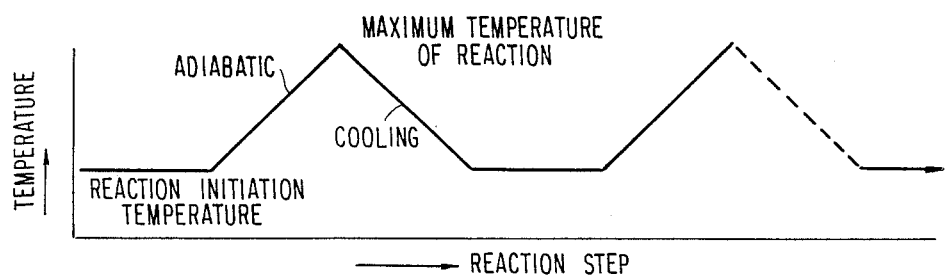

FIG. 2 shows the flow sheet of adiabatic reaction in which EDC is fed in two portions. Aqueous ammonia is introduced from a pipe 1, and EDC is introduced from a pipe 2. EDC is split into two portions, one of which is fed to a mixer 4 from the pipe 3 together with aqueous ammonia from the pipe 1. After thorough mixing, EDC and ammonia are introduced into a first adiabatic reactor 5. The reaction takes place mainly in this adiabatic reactor. The reaction product is introduced into a first cooler 11, in which it is cooled to the temperature at which aqueous ammonia and EDC were mixed first. (The cooling temperature may be properly changed according to the splitting ratio of EDC.) The reaction mixture discharged from the cooler 11 is then introduced into a second mixer 7 together with the remaining EDC introduced from a pipe 6. After thorough mixing, the mixture is introduced into a second adiabatic reactor 8. After reaction is completed (or the reaction temperature has reached the maximum temperature), the reaction product is cooled by a second cooler 12 to a proper temperature. Finally, the reaction product is transferred to the subsequent process through a pipe 10. On the other hand, an amine is added through a pipe 9 to at least one point between point A of the adiabatic reactor 5 where the overall conversion of EDC fed from the pipe 2 reaches 25% and point B of the adiabatic reactor 8 where the overall conversion of EDC reaches 85%.

Where EDC is fed in three or more portions, the mixer and adiabatic reactor should be added, as many as necessary according to the number of portions, after the cooler 11 or 12. An isothermal reactor may be placed between the mixer and the adiabatic reactor to help the dissolution of EDC.

The reaction mixture discharged through a pipe 10 from the final cooler 12 is treated as usual (such as addition of alkali, separation and recovery of excess ammonia, separation of sodium chloride, dehydration, and fractional distillation), and the desired polyethylenepolyamine is obtained.

The maximum temperature in each adiabatic reactor varies depending on the inlet temperature of the reactor, the number of portions of EDC, and other reaction conditions. It should be lower than 250° C., and preferably lower than 200° C. The inlet temperature of the reactor should be 60° to 180° C., and preferably 80° to 150° C.

The preferred concentration of aqueous ammonia introduced through the pipe 1, and the preferred molar ratio of EDC introduced through the pipe 2 to ammonia introduced through the pipe 1 are determined depending on the number of portions of EDC and the inlet temperature and maximum temperature of each adiabatic reactor. An amine introduced through the pipe 9 is added to EDC introduced through the pipe 2 in a molar ratio of 0.1 to 2.0, and preferably 0.1 to 1.0.

The invention is now described in more detail with reference to the following non-limitative examples.

EXAMPLE 1

A 1-liter stirred autoclave having an inside cooling coil was used as the reactor. The autoclave was provided with four detachable metering tanks.

At first, 200 g of water was charged into the reactor. Then, 236 g of liquid ammonia was fed from a cylinder. The reactor was heated to 100° C. with stirring. The vapor pressure of ammonia at 100° C. was 25 kg/cm$^2$G, and the concentration of ammonia in the liquid phase was calculated at 51.5 wt%.

92.9 g of EDC was forced all at once into the autoclave from the metering tank by the pressure of nitrogen (so that the molar ratio of ammonia to EDC was 13.3 in the liquid phase). The reaction temperature was kept at 100° C. by passing water through the cooling coil. Six minutes after the feeding of EDC, all the contents of the autoclave were transferred by pressure to a vessel containing 10 liters of water so that all the contents were dissolved in water. A part of the solution was taken from the vessel, and the content of Cl ion was determined by titration with silver nitrate. The percent conversion of EDC was calculated at 55% from the quantity of EDC fed and the quantity of Cl ion in the reactor.

The above-mentioned steps up to the feeding of EDC were repeated, and 6 minutes after the feeding of EDC, 28.7 g of EDA was added all at once from a metering tank by means of the pressure of the nitrogen. The molar ratio of EDA to EDC was 0.51.

Thirty minutes after the feeding of EDC, the reaction was completed and the reactor was cooled to room temperature. Excess free ammonia was released from the reactor and the reaction liquid was discharged. The content of Cl ion in the reaction liquid was determined by titration with silver nitrate. The percent conversion of EDC was calculated at 100%.

To the reaction liquid was added NaOH in a 5% excess stoichiometric quantity to neutralize and decompose NH$_4$Cl and amine hydrochloride in the reaction liquid. The reaction liquid was subjected to deammoniation and dehydration. The resulting amine solution was analyzed by gas chromatography to determine the quantities of amines formed and the quantities of cyclic amines formed as by-products in TETA and TEPA. The results were as follows:

EDA 23.3%, DETA 34.4%, TETA 18.7%, TEPA 8.6%, PEHA and higher polyamines 7.7%, P 2.7%, and N-AEP 4.6%. (Polyamines higher than DETA are mixtures of linear, branched, and cyclic amines.) It was found that the ratio of polyamines (excluding EDA, P and N-AEP) to EDA, PA/EDA, was 3.0. The ratio of the weight of two kinds of cyclic amines having four nitrogen atoms in TETA to the weight of linear TETA (CA-4/L-TETA) was 0.25. The ratio of the weight of two kinds of cyclic amines having five nitrogen atoms in TEPA to the weight of linear TEPA (CA-5/L-TEPA) was 0.48. These ratios indicate the quality of polyamines.

EXAMPLE 2

Example 1 was repeated except that EDA was added 3.5 minutes after the feeding of EDC. The percent conversion of EDC at the time of EDA addition was 30%. The quantities of amines formed were as follows: EDA 13.3%, DETA 36.3%, TETA 21.0%, TEPA 10.0%, PEHA and higher polyamines 11.0%, P 3.0%, and N-AEP 5.4%. The ratio of PA/EDA was 5.9; the ratio of CA-4/L-TETA was 0.29; and the ratio of CA-5/L-TEPA was 0.56.

EXAMPLE 3

Example 1 was repeated except that EDA was added 10 minutes after the feeding of EDC. The percent conversion of EDC at the time of EDA addition was 80%. The ratio of PA/ EDA was 1.2; the ratio of CA-4/L-TETA was 0.28; and the ratio of CA-5/L-TEPA was 0.54.

COMPARATIVE EXAMPLE 1

Example 1 was repeated except that EDA was added simultaneously with the feeding of EDC. The percent conversion of EDC at the time of EDA addition was 0%. The quantities of amines formed were as follows: EDA 2.4%, DETA 36.0%, TETA 23.5%, TEPA 12.0%, PEHA and higher polyamines 16.6%, P 3.0%, and N-AEP 6.5%. The ratio of PA/EDA was 36.7, or polyamines were formed in a large ratio. However, the ratio of CA-4/L-TETA was 0.40 and the ratio of CA-5/LTEPA was 0.75, or cyclic polyamines were also formed in a large ratio. This means that the polyamines formed are not satisfactory in quality.

COMPARATIVE EXAMPLE 2

Example 1 was repeated except that EDA was added 13 minutes after the feeding of EDC. The percent conversion of EDC at the time of EDA additior was 90%. The ratio of PA to EDA formed was 1.1. The ratio of CA-4/L-TETA was 0.31 and the ratio of CA-5/L-TEPA was 0.60. These data indicate that the ratio of polyamines formed to EDA is lower than that in Examples 1 to 3. Moreover, the polyamines formed were found poor in quality.

EXAMPLE 4

In the same manner as in Example 1, the reactor was charged with 310 g of water and 230 g of ammonia. The reactor was heated to 130° C. The concentration of ammonia in the liquid phase was calculated at 41 wt% from the vapor pressure of ammonia at 130° C. Then, 60 g of EDC was forced all at once into the reactor from the metering tank by means of the pressure of nitrogen. The reaction temperature was kept at 130° C. by passing water through the cooling coil.

Five minutes after the feeding of EDC (the fed EDC had reacted completely), 36.5 g of EDA was forced in and then 60 g of EDC was forced in again. The molar ratio of ammonia to the total EDC fed in the liquid phase was 10.4. The molar ratio of EDA added to the total EDC fed was 0.5. EDA was added when the overall conversion of the EDC fed had reached 50%.

The reaction was carried out at 130° C. for 5 minutes after the second feeding of EDC. Subsequently, the reactor was cooled to room temperature, and the reaction product was treated as in Example 1.

The ratio of PA formed to EDA was 2.6. The ratio of CA-4/L-TETA was 0.23 and the ratio of CA-5/L-TEPA was 0.41.

COMPARATIVE EXAMPLE 3

In the same manner as in Example 1, the reactor was charged with 206 g of water and 237 g of ammonia. The reactor was heated to 150° C. The concentration of ammonia in the liquid phase was calculated at 50.3 wt% from the vapor pressure of ammonia at 150° C. Then, 121 g of EDC was fed so that the molar ratio of ammonia to EDC in the liquid phase became 10.

An effort was made to keep the reaction temperature at 150° C. by passing water through the cooling coil; but the reactor temperature reached 175° C. due to excessive heat generation. Five minutes after the feeding of EDC (when the percent conversion of EDC had reached 100%), the reactor was cooled to room temperature by passing water through the cooling coil, and the reaction product was treated as in Example 1.

The ratio of PA formed to EDA was 1.1. The ratio of CA-4/L-TETA was 0.23 and the ratio of CA-5/L-TEPA was 0.41. In other words, the resulting polyamines were found good in quality, but the ratio of polyamines formed was low.

COMPARATIVE EXAMPLE 4

In the same manner as in Example 1, the reactor was charged with 138 g of water and 156.5 g of ammonia. The reactor was heated to 150° C. The concentration of ammonia in the liquid phase was calculated at 47 wt% from the vapor pressure of ammonia at 150° C. Then, 37.3 g of EDA was charged, and 123 g of EDC was fed at 150° C. so that the molar ratio of ammonia to EDC in the liquid phase became 6.0 and the molar ratio of EDA to EDC became 0.5. As EDC was fed, the reactor temperature reached 235° C. due to heat generation. Five minutes after the feeding of EDC, the reactor was cooled to room temperature, and the reaction product was treated as in Example 1.

It was found that a part of EDA added was converted to polyamines and no formation of EDA was observed. The ratio of CA-4/L-TETA was 0.35 and the ratio of CA-5/L-TEPA was 0.65. The resulting polyamines were found to contain a large amount of cyclic polyamines.

EXAMPLE 5

In the same manner as in Example 1, the reactor was charged with 200 g of water and 236 g of ammonia. 46.5 g of EDC (which is one half of the total EDC to be fed) was charged at 100° C. Reaction was carried out at 100° C. for 30 minutes (for complete reaction of EDC fed).

The remaining 46.5 g of EDC was fed at 100° C. Immediately after that, 28.7 g of EDA was added and reaction was carried out again at 100° C. for 30 minutes. The reaction product was treated as in Example 1. The molar ratio of ammonia to total EDC in the liquid phase was 13.3 and the molar ratio of EDA to total EDC was 0.51. The overall conversion of EDC at the time of EDA addition was 50%.

The ratio of PA formed to EDA was 4.3. The ratio of CA-4/L-TETA was 0.25 and the ratio of CA-5/L-TEPA was 0.50.

COMPARATIVE EXAMPLE 5

In the same manner as in Example 1, the reactor was charged with 200 g of water and 236 g of ammonia. 46.5 g of EDC (which is one half of the total EDC to be fed) was charged at 100° C. Reaction was carried out for 30 minutes, with the reactor temperature controlled by passing water through the cooling coil.

The remaining 46.5 g of EDC was fed, and reaction was carried out again at 100° C. for 30 minutes. The reactor was cooled to room temperature, and the reaction product was treated as in Example 1.

The molar ratio of ammonia to total EDC in the liquid phase was 13.3 and the concentration of ammonia was 51.5 wt%. EDC was added in two portions, without the addition of EDA.

The ratio of PA formed to EDA was 1.2. The ratio of CA-4/L-TETA was 0.35 and the ratio of CA-5/L-TEPA was 0.66. The ratio of polyamines formed was lower than that in Example 5, and the resulting polyamines were found to be poor in quality due to the high ratio of cyclic amines.

COMPARATIVE EXAMPLE 6

Example 5 repeated except that EDA was fed 4 minutes after the first feeding of EDC (when the percent conversion of EDC fed first had reached 36%). In other words, EDA was added when the overall conversion of EDC fed reached 18%.

The ratio of PA formed to EDA was 11.3. The ratio of CA-4/L-TETA was 0.33 and the ratio of CA-5/L-TEPA was 0.65.

EXAMPLE 6

In the same manner as in Example 1, the reactor was charged with 200 g of water and 236 g of ammonia. 65.1 g of EDC (which is 70% of the total EDC 93 g to be fed) was charged at 100° C. Reaction was carried out for 30 minutes until the EDC fed reacted completely. Then, 28.7 g of EDA was added, and the reactor was heated to 120° C., and the remaining 27.9 g of EDC (30% of total EDC) was fed. The reaction was carried out at 120° C. for 30 minutes. The reactor was cooled to room temperature, and the reaction product was treated as in Example 1.

The concentration of ammonia was 51.5 wt%. The molar ratio of ammonia to total EDC in the liquid phase was 13.3 and the molar ratio of EDA to total EDC was 0.51. The overall conversion of EDC at the time of EDA addition was 70%.

The ratio of PA formed to EDA was 2.4. The ratio of CA-4/L-TETA was 0.23 and the ratio of CA-5/L-TEPA was 0.48.

EXAMPLE 7

In the same manner as in Example 1, the reactor was charged with 326 g of water and 200 g of ammonia. The reactor was heated to 120° C. The concentration of ammonia in the liquid phase was calculated at 37.5 wt% from the vapor pressure of ammonia. Then, 39.0 g of EDC was fed, and the reaction was carried out at 120° C. for 10 minutes. Then, 36.0 g of EDA was added and 39.0 g of EDC was added for the second time. The reaction was carried out at 120° C. for 10 minutes. Finally, 39.0 g of EDC was fed for the third time. The reaction was carried out for 10 minutes. After the reaction was complete, the reactor was cooled to room temperature, and the reaction product was treated as in Example 1.

The molar ratio of ammonia to total EDC in the liquid phase was 9.7, and the molar ratio of EDA to total EDC was 0.51. The overall conversion of EDC at the time of EDA addition was 33.3%.

The quantities of amines formed were EDA 14.2%, DETA 34.9%, TETA 21.3%, TEPA 10.1%, PEHA and higher polyamines 11.9%, P 2.8%, and N-AEP 4.8%.

The ratio of PA to EDA was 5.5. The ratio of CA-4/L-TETA was 0.25 and the ratio of CA-5/L-TEPA was 0.50.

EXAMPLE 8

A 300-ml autoclave having an inside cooling coil and electromagnetic stirrer was used as the reactor. In the same manner as in Example 1, the reactor was charged with 56 g of water and 72.9 g of ammonia. The reactor was heated to 120° C. The concentration of ammonia in the liquid phase was calculated at 49 wt% from the vapor pressure of ammonia at 120° C. 32.4 g of EDC was fed (so that the molar ratio of ammonia to EDC was 9.8 in the liquid phase).

As EDC was fed, the reactor temperature rose due to reaction heat; but no temperature control was made and the reactor temperature was allowed to rise freely. One minute after the feeding of EDC (when the percent conversion of EDC had reached 50%), 5.9 g of EDA was fed (with the molar ratio of EDA to EDC being 0.3). The reaction was continued. One minute and fifty seconds after the feeding of EDC, the temperature in the reactor reached a maximum of 178° C. The reactor was cooled to room temperature, and the reaction product was treated as in Example 1.

The ratio of PA formed to EDA was 2.5. The ratio of CA-4/L-TETA was 0.24 and the ratio of CA-5/L-TEPA was 0.45.

EXAMPLE 9

In the same manner as in Example 1, the reactor was charged with 206 g of water and 237 g of ammonia. The reactor was heated to 90° C. The concentration of ammonia in the liquid phase was calculated at 52.5 wt% from the vapor pressure of ammonia at 90° C. 60 g of EDC was fed. As EDC was fed, the reactor temperature rose due to reaction heat; but no temperature control was made and the reactor temperature was allowed to rise freely. Five minutes after the feeding of EDC, the temperature in the reactor reached a maximum of 130° C. The reactor was cooled to 90° C. by passing water through the cooling pipe. 37.6 g of EDA was added and 60 g of EDC was fed at 90° C. As EDC was fed for the second time, the reactor temperature rose again to a maximum of 129° C. After that, the reactor was cooled to room temperature by passing water through the cooling coil, and the reaction product was treated as in Example 1.

The molar ratio of ammonia to total EDC in the liquid phase was 11, and the molar ratio of EDA to total EDC was 0.50. The overall conversion of EDC at the time of EDA addition was 50%.

The quantities of amines formed were EDA 16.1%, DETA 34.2%, TETA 21.3%, TEPA 9.6%, PEHA and higher polyamines 11.2%, P 3.0%, and N-AEP 4.6%.

The ratio of PA to EDA was 4.7. The ratio of CA-4/L-TETA was 0.26 and the ratio of CA-5/L-TEPA was 0.52.

EXAMPLE 10

In the same manner as in Example 9, the reactor was charged with 138 g of water and 156 g of ammonia. 79 g of EDC was fed at 125° C. One minute and fifteen seconds after the feeding of EDC, the maximum temperature of 184° C. was reached. The reactor was cooled to 125° C. Then, 48 g of EDA was added thereto, and 79 g of EDC was fed for the second time at 125° C. One minute after the second feeding of EDC, the maximum temperature of 177° C. was reached. The reactor was cooled to room temperature, and the reaction product was treated as in Example 1.

The concentration of ammonia in this Example was 47.9 wt%. The molar ratio of ammonia to total EDC in the liquid phase was 4.7, and the molar ratio of EDA to total EDC was 0.50. The overall conversion of EDC at the time of EDA addition was 50%.

The ratio of PA formed to EDA was 104. The ratio of CA-4/L-TETA was 0.23 and the ratio of CA-5/L-TEPA was 0.46.

EXAMPLE 11

In the same manner as in Example 9, the reactor was charged with 232 g of water and 257 g of ammonia. 45 g of EDC was fed at 140° C. One minute and fifteen seconds after the feeding of EDC, the maximum temperature of 165° C. was reached. The reactor was cooled to 150° C. 45 g of EDC was fed again, and immediately after that 54.7 g of EDA was added. One minute after the second feeding of EDC, the maximum temperature of 171° C. was reached. The reactor was cooled to room temperature, and the reaction product was treated as in Example 1.

The concentration of ammonia in this Example was 50 wt%. The molar ratio of ammonia to total EDC in the liquid phase was 14.9, and the molar ratio of EDA to total EDC was 1.0. The overall conversion of EDC at the time of EDA addition was 50%.

The ratio of PA formed to EDA was 33. The ratio of CA-4/L-TETA was 0.12 and the ratio of CA-5/L-TEPA was 0.25.

EXAMPLE 12

In the same manner as in Example 9, the reactor was charged with 206 g of water and 236 g of ammonia. 61 g of EDC was fed at 170° C. 30 seconds after the feeding of EDC, the maximum temperature of 207° C. was reached. The reactor was cooled to 170° C. 37 g of EDA was added and 61 g of EDC was fed. After the maximum temperature of 205° C. was reached, the reactor was cooled to room temperature, and the reaction product was treated as in Example 1.

The concentration of ammonia in this Example was 49.3 wt%. The molar ratio of ammonia to total EDC in the liquid phase was 9.5, and the molar ratio of EDA to total EDC was 0.5. The overall conversion of EDC at the time of EDA addition was 50%.

The ratio of PA formed to EDA was 2.9. The ratio of CA-4/L-TETA was 0.17 and the ratio of CA-5/L-TEPA was 0.32.

EXAMPLE 13

In the same manner as in Example 9, the reactor was charged with 206 g of water and 237 g of ammonia. 61 g of EDC was fed at 130° C. 40 seconds after the feeding of EDC, 38 g of EDA was added. The percent conversion of EDC fed at the time of EDA addition was 60%. One minute and eighteen seconds after the feeding of EDC, the maximum temperature of 163° C. was reached. The reactor was cooled to 130° C., and 61 g of EDC was fed again. One minute and six seconds after the second feeding of EDC, the maximum temperature of 162° C. was reached. After that the reactor was cooled to room temperature, and the reaction product was treated as in Example 1.

The concentration of ammonia in this Example was 50.6 wt%. The molar ratio of ammonia to total EDC in the liquid phase was 10, and the molar ratio of EDA to total EDC was 0.51. The overall conversion of EDC at the time of EDA addition was 30%.

The ratio of PA formed to EDA was 4.6. The ratio of CA-4/L-TETA was 0.24 and the ratio of CA-5/L-TEPA was 0.45.

COMPARATIVE EXAMPLE 7

Example 13 was repeated, except that EDA was added before EDC was fed for the first time. In other words, the overall conversion of EDC fed was 0% at the time of EDA addition.

The maximum temperature after the first feeding of EDC was 162° C., and the maximum temperature after the second feeding of EDC was 163° C.

The ratio of PA formed to EDA was 34. The ratio of CA-4/L-TETA was 0.33 and the ratio of CA-5/L-TEPA was 0.60.

COMPARATIVE EXAMPLE 8

Example 13 was repeated, except that EDA was added when the reactor temperature reached a maximum of 162° C. as the result of the second feeding of EDC. The reactor was allowed to stand without cooling for 5 minutes after the addition of EDA. The reactor temperature fell slowly and reached 125° C. after 5 minutes. The overall conversion of EDC fed was 98% at the time of EDA addition.

The ratio of PA formed to EDA was 1.1. The ratio of CA-4/L-TETA was 0.30 and the ratio of CA-5/L-TEPA was 0.52.

EXAMPLE 14

In the same manner as in Example 9, the reactor was charged with 145 g of water and 175 g of ammonia. 40 g of EDC was fed at 135° C. One minute after the feeding of EDC, the maximum temperature of 167.5° C. was reached. The reactor was cooled to 135° C., and 40 g of EDC was fed again. One minute later, the reactor temperature rose to 165° C. The reactor was cooled again to 135° C., and 37 g of EDA was added and 40 g of EDC was fed for the third time. Thirty seconds after the third feeding of EDC, the temperature rose to 163° C. After that the reactor was cooled to room temperature, and the reaction product was treated as in Example 1.

The concentration of ammonia in this Example was 50 wt%. The molar ratio of ammonia to total EDC in the liquid phase was 7, and the molar ratio of EDA to total EDC was. 0.5. The overall conversion of EDC at the time of EDA addition was 66%.

The ratio of PA formed to EDA was 2.9. The ratio of CA-4/L-TETA was 0.23 and the ratio of CA-5/L-TEPA was 0.47.

While the invention has been described in detail and with reference to specific embodiments thereof, it will be apparent to one skilled in the art that various changes and modifications can be made therein without departing from the spirit and scope thereof.

What is claimed is:

1. A process for producing polyethylene polyamines by reacting ethylene dichloride and aqueous ammonia wherein feed of the ethylene dichloride to the aqueous ammonia is separated into at least two separate additions, which comprises initially reacting ethylene dichloride with aqueous ammonia by feeding from 30 to 80% of the total of the ethylene dichloride to be fed to the process and reacting substantially all of said 30 to 80% of the total of the ethylene dichloride to be fed to the process with said aqueous ammonia, adding thereto at least one amine; and then feeding the remaining ethylene dichloride to continue the reaction of said ethylene dichloride and said aqueous ammonia to said polyethylene polyamines, thereby completing the reaction of the whole of said ethylene dichloride.

2. A process as claimed in claim 1, wherein the reaction is carried out isothermally at a temperature in the range of from 60° to 250° C.

3. A process as claimed in claim 1, wherein said amine is an ethyleneamine.

4. A process as claimed in claim 3, wherein said ethyleneamine is ethylenediamine.

5. A process as claimed in claim 1, wherein the molar ratio of said amine to the starting ethylene dichloride is in the range of from 0.1 to 2.0.

6. A process as claimed in claim 1, wherein the concentration of said aqueous ammonia is in the range of from 30 to 70% by weight, and the molar ratio of ammonia to the starting ethylene dichloride is in the range of from 3 to 20.

7. A process as claimed in claim 1, wherein the reaction is carried out adiabatically at a temperature in the range of from 60° to 250° C.

* * * * *